United States Patent [19]

Hatanaka et al.

[11] Patent Number: 4,980,478

[45] Date of Patent: Dec. 25, 1990

[54] PROCESS FOR PRODUCING SUBSTITUTED VINYL PYRIDINE DERIVATIVES

[75] Inventors: Chitoshi Hatanaka, Nagaokakyo; Sigel Nuwa, Kawanishi; Satoru Oi, Nara, all of Japan

[73] Assignee: Takeda Chemical Industries, Ltd., Osaka, Japan

[21] Appl. No.: 333,082

[22] Filed: Apr. 4, 1989

[51] Int. Cl.⁵ .................. C07D 213/28; C07D 213/57; C07D 401/06; C07D 405/06
[52] U.S. Cl. ................................ 546/342; 546/255; 546/256; 546/268; 546/270; 546/283; 546/330; 546/333; 546/337; 546/342; 546/343; 546/344
[58] Field of Search ............... 546/268, 270, 283, 284, 546/342, 343, 344, 330, 333, 337, 256, 255

[56] References Cited

U.S. PATENT DOCUMENTS 4,518,602  5/1985  Terao et al. .................. 514/332

FOREIGN PATENT DOCUMENTS 0098690  1/1984  European Pat. Off. ........... 514/332
0135316  3/1985  European Pat. Off. ........... 546/276
0150433  8/1985  European Pat. Off. ........... 546/340
0173172  3/1986  European Pat. Off. ........... 546/276
60-226611  4/1987  Japan ............................ 546/341

*Primary Examiner*—Alan L. Rotman
*Attorney, Agent, or Firm*—Wegner, Cantor, Mueller & Player

[57] ABSTRACT

An improved process for producing a substituted vinyl pyridine compound of the general formula:

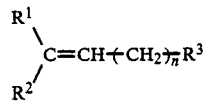

wherein $R^1$ is pyridyl group; $R^2$ is an optionally substituted aromatic or heterocyclic group; $R^3$ is a lower alkyl group, hydroxymethyl group, nitroxymethyl group, a nitrogen containing 5 membered ring-methyl group, an acetal-methyl group, a trialkylsilyloxymethyl group, an alkyl- or aryl-sulfonyloxymethyl group, an alkyl- or aryl-sulfonylaminocarbonyloxymethyl group, an acyloxymethyl group, an alkoxycarbonyloxymethyl group, a halogenomethyl group, an alkoxymethyl group, an aryl-oxymethyl group, cyano group, an optionally substituted carbamoyl group, an optionally substituted carbamoyloxymethyl group, an optionally substituted thiocarbamoyloxymethyl group, carboxyl group or an alkoxycarbonyl group; and n is an integer of 1 to 22, which comprises reacting a compound of the general formula:

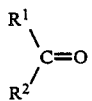

wherein $R^1$ and $R^2$ are as defined above, with a compound of the general formula:

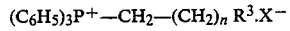

wherein $R^3$ is as defined above and X is a halogen atom, in a tertiary alcohol in the presence of a metallic hydride or a tertiary alkoxide of an alkali metal.

13 Claims, No Drawings

PROCESS FOR PRODUCING SUBSTITUTED VINYL PYRIDINE DERIVATIVES

FIELD OF THE INVENTION

The present invention relates to a process for producing substituted vinyl pyridines which have specific activities for inhibiting thromooxane $A_2$ ($TXA_2$) synthetase.

BACKGROUND OF THE INVENTION

A process for producing substituted vinyl pyridines having inhibitory activity against $TXA_2$ synthetase has been already known (Japanese Patent Laid Open Publication No. 219162/1983). However, when this process is studied in detail, the production conditions have various problems from the viewpoint of safety and particularly, in the case of expansion of the production scale, there may be a danger that a serious accident would happen.

That is, in Japanese Patent Laid Open Publication No. 219162/1983, in order to produce a substituted vinyl pyrdine compound of the general formula:

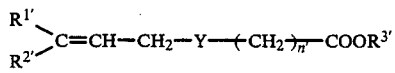

wherein $R^{1'}$ is pyridyl group; $R^{2'}$ is phenyl group optionally having a lower alkoxy group, a lower alkyl group, a halogen atom, trifluoromethyl group, a lower alkenyl group or methylenedioxy group, thienyl group, furyl group, naphthyl group, benzothienyl group or pyridyl group; Y is methylene group; $R^{3'}$ is hydrogen atom or a lower alkyl group; and n' is an integer of 0 to 6, a compound of the general formula:

wherein $R^{1'}$ and $R^{2'}$ are as defined above, is reacted with a compound of the general formula:

wherein X is a halogen atom; and $R^{3'}$ and n are as defined above, in a solvent in the presence of a base. It is disclosed that, as this base, there can be used n-butyl lithium, sodium hydride, potassium tertiary butoxide and the like and, among them, n-butyl lithium and sodium hydride are preferred. As the solvent, for example, ether, tetrahydrofuran, dimethylformamide, dimethylsulfoxide or a mixed solvent of two or more of these solvents is disclosed There are disclosed that this reaction is preferably carried out under the atmosphere of a dried inert gas (e.g., nitrogen gas, helium gas or the like), and that the reaction temperature is −10° C. to 50° C., preferably 0° C. to 30° C., and the progress of the reaction can be monitored by observing disappearance of the characteristic color of phospholane, and the reaction is normally completed within about 1 to 6 hours.

In this process, with regard to most of combinations of these solvents and bases, danger has been hitherto pointed out and accidents such as explosion and the like have been reported. Examples of these accidents were as follows: (1) It has been reported that, when sodium hydride or an alkoxide such as sodium methoxide or the like was used in dimethylformamide, dimethylformamide was exothermically decomposed to produce carbon monoxide as a by-product, which induced runaway reaction ["Chemistry and Industry", 17, Feb., 1984, 134; "Chem. Eng. News", 1982, 60 (28), 5; "Chem. Eng. News", 1982, 60, Jul., 12, 5; and "Chem. Eng. News", 60, September 13, 5]; (2) It has been reported that, when the reaction was carried out by using sodium hydride in dimethylsulfoxide, dimethylsulfinyl anion was produced, which caused explosion ["Chem. Eng. News", 1966, 44, April 11, 48; and "Chem. Eng. News", 1966, 44, June 13, 7]; and (3) It has been reported that, when a hydride was refluxed in tetrahydrofuran, explosion was caused (this has been reported with regard to calcium hydride) ["Chem. Eng. News", 1987, 56, February 6, 3; and "Chem. Eng. News", 1987, April 17, 68]. Further, to use a large amount of a hydride which generates hydrogen in a solvent having a low flash point such as ethyl ether or the like is accompanied with the same danger as those described above, and n-butyl lithium is extremely sensitive to moisture, which renders its handling disadvantageous.

OBJECTS OF THE INVENTION

In order to improve the above process to obtain an industrial process which is perfect even from the viewpoint of safety, the present inventors have studied intensively. As the results, there has been found certain reaction conditions under which the above object can be fully attained by using combinations of solvents and bases for which no accident has been reported and no special danger has not been pointed out so far as they are handled with caution strictly, and the objective substituted vinyl pyridines can be produced in a high yield and safely.

That is, the main object of the present invention is to provide an improved industrial process for producing the substituted vinyl pyridines.

This object as well as other objects and advantages of the present invention will become apparent to those skilled in the art from the following description.

SUMMARY OF THE INVENTION

According to the present invention, there is provided a process for producing a substituted vinyl pyridine compound of the general formula:

wherein $R^1$ is pyridyl group; $R^2$ is an optionally substituted aromatic or heterocyclic group; $R^3$ is a lower alkyl group, hydroxymethyl group, nitroxymethyl group, a nitrogen containing 5 membered ring-methyl group, an acetal-methyl group, a trialkylsilyloxymethyl group, an alkyl- or arylsulfonyloxymethyl, an alkyl- or aryl-sulfonylaminocarbonyloxymethyl group, an acyloxymethyl group, an alkoxycarbonyloxymethyl group, a halogenomethyl group, an alkoxymethyl group, an aryl-oxymethyl group, cyano group, an optionally substituted carbamoyl group, an optionally substituted carbamoyloxymethyl group, an optionally substituted thiocarbamoyloxymethyl group, carboxyl group or an alkoxycarbonyl group; and n is an integer of 1 to 22, which comprises reacting a compound of the general formula:

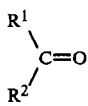

$$\begin{matrix} R^1 \\ \phantom{R}\diagdown \\ \phantom{RR}C=O \\ \phantom{R}\diagup \\ R^2 \end{matrix} \qquad (II)$$

wherein $R^1$ and $R^2$ are as defined above, with a compound of the general formula:

$$(C_6H_5)_3P^+\text{-}(CH_2\text{---}CH_2)_nR^3\cdot X^- \qquad (III)$$

wherein $R^3$ and n are as defined above; and X is a halogen atom, in a tertiary alcohol in the presence of a metallic hydride or a tertiary alkoxide of alkali metal.

DETAILED DESCRIPTION OF THE INVENTION

In the above general formulas (I), (II) and (III), pyridyl group represented by $R^1$ may be any of 2-pyridyl, 3-pyridyl and 4-pyridyl. Among them, 3-pyridyl is preferable. As the aromatic group represented by $R^2$, there are, for example, an aryl group such as phenyl, naphthyl (α-naphthyl, β-naphthyl) and the like and, as the heterocyclic ring group, there are thienyl (2-thienyl, 3-thienyl), furyl (2-furyl, 3-furyl), pyridyl (2-pyridyl, 3-pyridyl, 4-pyridyl), benzothienyl (2-benzothienyl, 3-benzothienyl, 4-benzothienyl, 5-benzothienyl, 6-benzothienyl, 7-benzothienyl) and the like. Both aromatic group and heterocyclic ring group may have a substituent at any position. As the substituent, there are, for example, a lower alkoxy group (e.g., those having 1 to 4 carbon atoms such as methoxy, ethoxy, n-propoxy, i-propoxy, n-butoxy, i-butoxy, t-butoxy and the like), a lower alkyl (e.g., those having 1 to 5 carbon atoms such as methyl, ethyl, n-propyl, i-propyl, n-butyl, i-butyl, t-tutyl, n-pentyl and the like), trifluoromethyl, a lower alkenyl (e.g., those having 2 to 5 carbon atoms such as vinyl, allyl, pentenyl and the like), a halogen (fluorine, chlorine, bromine, iodine), methylenedioxy and the like. As the lower alkyl group represented by R3, there are, for example, those having 1 to 4 carbon atoms such as methyl, ethyl, n-propyl, i-propyl, n-butyl, i-butyl, t-butyl and the like. As the nitrogen containing 5. membered ring-methyl group, there are, for example, methyl group of which hydrogen is substituted with a 5 membered ring group having 2 to 4 nitrogen atoms such as imidazolylmethyl (1-imidazolylmethyl, 2-imidazolylmethyl), triazolylmethyl (1-triazolylmethyl, 3-triazolylmethyl, 5-triazolylmethyl), tetrazolylmethyl (1-tetrazolylmethyl, 5-tetrazolelmethyl) and the like. As the acetal-methyl group, there are, for example, 2-tetrahydropyranyloxymethyl, 2-tetrahydrofuryloxymethyl and the like. As the trialkylsilyloxymethyl group, there are, for example, dimethyltertiary-butylsilyloxymethyl and the like. As the alkyl- or aryl-sulfonyloxymethyl group, there are, for example, methanesulfonyloxymethyl, p-toluenesulfonyloxymethyl and the like. As the alkyl- or aryl-sulfonylaminocarbonyloxymethyl group, there are, for example, methanesulfonylaminocarbonyloxymethyl, p-toluenesulfonylaminocarbonyloxymetyl and the like. As the acyloxymethyl group, there are groups represented by the formula: $R^4COOCH_2$—[wherein $R^4$ is hydrogen, alkyl having 1 to 6 carbon atoms (methyl, ethyl, n-propyl, i-propyl, n-butyl, i-butyl, n-pentyl, i-pentyl, n-hexyl and the like) or pyridyl (2-pyridyl, 3-pyridyl, 4-pyridyl)]. As the alkoxycarbonyloxymethyl group, there are, for example, those having 3 to 8 carbon atoms such as methoxycarbonyloxymethyl, ethoxycarbonyloxymethyl, n-propoxycarbonyloxymethyl, i-propoxycarbonyloxymethyl, n-butoxycarbonyloxymethyl, i-butoxycarbonyloxymethyl, n-pentyloxycarbonyloxymethyl, n-hexyloxycarbonyloxymethyl and the like. As the halogenomethyl group, there are, for example, fluorometyl, chloromethyl, bromomethyl, iodomethyl and the like. As the alkoxymethyl group, there are, for example, lower alkoxymethyl having 2 to 5 carbon atoms such as methoxymethyl, ethoxymethyl, n-propoxymethyl, i-propoxymethyl, n-butoxymethyl, i-butoxymethyl and the like. As the aryloxymethyl group, there are, for example, those having 7 to 9 carbon atoms such as phenyloxymetyl, 2-methylphenyloxymethyl, 3-methylphenyloxymethyl, 4-methylphenyloxymethyl, 2,4-dimethylphenyloxymethyl, 3,4-dimethylphenyloxymethyl and the like. As the optionally substituted carbamoyl group, there are those represented by the formula:

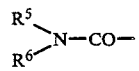

$$\begin{matrix} R^5 \\ \phantom{R}\diagdown \\ \phantom{RR}N\text{---}CO\text{---} \\ \phantom{R}\diagup \\ R^6 \end{matrix}$$

wherein $R^5$ and $R^6$ are the same or different and are alkyl having 1 to 6 carbon atoms (e.g., methyl, ethyl, n-propyl, i-propyl, n-butyl, i-butyl, t-butyl, n-pentyl, i-pentyl, n-hexyl, i-hexyl and the like) or aryl having 6 to 8 carbon atoms (phenyl, 2-methylphenyl, 3-methylphenyl, 4-methylphenyl, 2,4-dimethylphenyl, 3,4-dimethylphenyl and the like). As the optionally substituted carbamoyloxymethyl group, there are those represented by the formula:

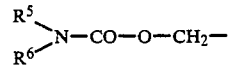

$$\begin{matrix} R^5 \\ \phantom{R}\diagdown \\ \phantom{RR}N\text{---}CO\text{---}O\text{---}CH_2\text{---} \\ \phantom{R}\diagup \\ R^6 \end{matrix}$$

wherein $R^5$ and $R^6$ are as defined above. As the optionally substituted thiocarbamoyloxymethyl group, there are those represented by the formula:

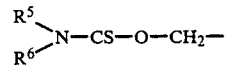

$$\begin{matrix} R^5 \\ \phantom{R}\diagdown \\ \phantom{RR}N\text{---}CS\text{---}O\text{---}CH_2\text{---} \\ \phantom{R}\diagup \\ R^6 \end{matrix}$$

wherein $R^5$ and $R^6$ are as defined above. And, as the alkoxycarbonyl group, there are, for example, those having 2 to 5 carbon atoms such as methoxycarbonyl, ethoxycarbonyl, n-propoxycarbonyl, i-propoxycarbonyl, n-butoxycarbonyl, i-butoxycarbonyl, t-butoxycarbonyl and the like.

As $R^3$, carbonyl, methyl and a lower alkoxycarbonyl having 2 to 5 carbon atoms are preferable. n is an integer of 1 to 22, preferably an integer of 3 to 8 and the most preferably 3 to 6.

The representative examples of the compounds of the general formula (I) includes those wherein $R^1$ is 3-pyridyl, $R^2$ is phenyl, $R^3$ is carboxyl, a lower alkoxycarbonyl group having 2 to 5 carbon atoms or methyl and n is an integer of 3 to 8, preferably, 3 to 6.

Thus, in the process of the present invention, a tertiary alcohol is used as the reaction solvent and a metallic hydride or a tertiary alkoxide of alkali metal is used as the base.

It has been found that, among alcohols, when a primary alcohol is used, the objective product is not obtained and, when a secondary alcohol is used, the objective product is obtained only in a low yield. Further, it has been also found that, especially, among the metal alkoxide, when a primary alkoxide such as sodium ethoxide is used, although the objective product is produced, the yield is low.

According to the reaction of the present invention, two kinds of geometrical isomers (E and Z isomers) are normally produced. However, there are many cases wherein either of the isomers is useful. For example, E isomer having a biological activity is of importance in the case of 7-phenyl-7-(3-pyridyl)-6-heptenoic acid. Therefore, the reaction conditions having selectivity are desired. In the case of 7-phenyl-7-(3-pyridyl)-6-heptenoic acid, it is difficult to prepare predominantly one of the isomers because of a structural similarity of two substituents at 7-position. For example, when the synthesis is carried out under the conditions as described in Japanese Patent Laid Open Publication No. 219162/1983, Z isomer is produced in such a degree that the amount thereof is somewhat greater than that of E isomer. However, it has been unexpectedly found that, when the reaction is carried out according to the present invention, in the case of the compound of the general formula (I) wherein $R^1$ is pyridyl and $R^2$ is phenyl, the amount of E isomer produced is clearly greater than that of Z isomer and its selectivity becomes more significant at a low temperature of not higher than 10° C., and that, when acetonitrile is used as a solvent, to the contrary, the production of Z isomer becomes significant.

Hereinafter, the process of the present invention are further explained in detail.

As the tertiary alcohol to be used as the reaction solvent, there can be used any tertiary alcohols such as tertiary butanol, tertiary amyl alcohol and the like. If desired, the tertiary alcohol can also be used in combination with other solvents such as aromatic hydrocarbons, aliphatic saturated hydrocarbons, aliphatic ethers and the like in view of solubility and operating properties of the reactants. As the aromatic hydrocarbons to be mixed with the tertiary alcohol, there are, for example, toluene, benzene, xylene and the like. As the aliphatic saturated hydrocarbons, there are hexane, cyclohexane and the like and, as the aliphatic ethers, there are ethyl ether, isopropyl ether, diethylene glycol dimethyl ether and the like. Among the solvent to be mixed with the tertiary alcohol, toluene, benzene, isopropyl ether and cyclohexane are preferable. As the mixed solvent, a mixture of tertiary-butanol and toluene is particularly properable. Regarding the selection of these solvents, they can be used alone or in combination of two or more thereof according to solubility of the compounds represented by the general formulas (I), (II) and (III), operating properties and the like. Any mixing ratio can be employed by taking into consideration of solubility of the starting materials and the product, operating properties, economy, production ratio of isomers and the like and, normally, it is preferred that these solvent are used in an amount of not more than 50% based on the tertiary alcohol.

As the metallic hydride to be used as the base, there are hydrides of alkali metals or alkaline earth metals such as sodium hydride, potassium hydride, calcium hydride and the like. As the tertiary alkoxide of alkali metal, there can be used potassium tertiary butoxide, sodium tertiary butoxide, potassium tertiary amyloxide or the like. Among these bases, sodium hydride and potassium tertiary butoxide are preferable. As the potassium tertiary alkoxide, in addition to the comercially available potassium tertiary alkoxide, there can be used a potassium tertiary alkoxide-containing tertiary alcohol solution obtained by reaction of the tertiary alcohol with metallic potassium, or a potassium tertiary alkoxide-containing tertiary alcohol solution obtained by dehydration of the tertiary alcohol and potassium hydroxide as it is. The amount of the base to be used is preferably 2.0 to 3.0-fold mol as much as that of the compound represented by the general formula (III).

Although the reaction temperature can be selected in any range between −30° C. and the boiling point of the reaction solvent to be used, the reaction is preferably carried out at the temperature of −10° to 90° C. by taking into consideration of the reaction time and production ratio of E isomer and Z isomer. the reaction time is normally 1 to 3 hours. In the present invention, it is preferred that the reaction is carried out under the atmosphere of a dried inert gas (e.g., nitrogen gas, helium gas or the like).

As described hereinabove, according to the present invention, the objective substituted vinyl pyridines can be produced in an industrial scale in a good yield without danger as in a conventional progress.

The following Examples and Comparative Examples further illustrates the present invention in detail but are not to be construed to limit the scope thereof.

EXAMPLE 1

A mixture of 3-benzoylpyridine (33.0 g, 0.18 mol), 5-carboxypentyltriphenylphosphonium bromide (84.0 g, 0.184 mol) and tertiary butanol (540 ml) was heated to about 60° C. and to the mixture was added sodium hydride (60% in oil, 15.8 g, 0.396 mol) by several portions with stirring under a $N_2$ atmosphere. After stirring at 60° to 70° C. for an hour, tertiary butanol was distilled off under reduced pressure. To the residue were added toluene (80 ml) and water (160 ml) and layers were separated. (E)- and (Z)-7-phenyl-7-(3-pyridyl)-6-heptenoic acids in the aqueous layer were determined by high performance liquid chromatography with authentic samples of E isomer and Z isomer. As the results, it was confirmed that 24.9 g of E isomer and 24.7 g of Z isomer (E : Z=50.2:49.8), total 49.6 g (yield: 98.8%, yield of E isomer: 49.6%) were contained.

EXAMPLE 2

A mixture of 3-benzoylpyridine (16.5 g, 90 mmol), 5-carboxypentyltriphenylphosphonium bromide (42.0 g, 92 mmol), tertiary butanol (120 ml) and toluene (30 ml) was heated to about 60° C. and to the mixture was added potassium tertiary butoxide (25.3 g, 198 mmol) by several portions. After stirring at 60° to 70° C. for an hour, the reaction mixture was cooled and water (480 ml) was added. After washing with toluene (100 ml), (E)- and (Z)-7-phenyl-7-(3-pyridyl)-6-heptenocic acids in the aqueous layer were determined according to the same manner as described in Example 1. As the results, it was confirmed that 12.9 g of E isomer and 10.7 g of Z isomer, total 49.6 g (yield: 93.1%) were contained (E:Z=54.8:45.2, yield of E isomer: 93.1%).

When the reaction was carried out according to the same manner as described above at the reaction temperature of 20° to 30° C., 23.0 g of (E+Z)-7-phenyl-7-(3-pyridyl)-6-heptenoic acid was produced after one hour (yield: 95.7%, E:Z=58.3:41.7, yield of E isomer: 55.8%).

Further, when the reaction was carried out according to the same manner as described above at the reaction temperature of 5° to 10° C., 23.6 g of (E+Z)-7-phenyl-7-(3-pyridyl)-6-heptenoic acid gas produced after 3 hours (yield: 95.2%, E : Z=61.0:39.0, yield of E isomer: 58.1%).

EXAMPLE 3

To a mixture of 3-benzoylpyridine (1.65 g, 9 mmol), 5-carboxypentyltriphenylphosphonium bromide (4.2 g, 9.2 mmol), tertiary butanol (15 ml) and toluene (5 ml) was added sodium hydride (60% in oil, 0.74 g, 18.4 mmol) by several portions with stirring under a $N_2$ atmosphere. After completion of addition, the mixture was stirred at 20° to 30° C. for 2 hours. After cooling, to the reaction mixture were added water (50 ml) and toluene (30 ml), and layers were separated. (E)- and (Z)-7-phenyl-7-(3-pyridyl)-6-heptenoic acids in the aqueous layer were determined according to the same manner as that described in Example 1. As the results, 1.20 g of E isomer and 1.18 g of Z isomer (E : Z=50.3:49.7), total 2.38 g (yield: 94.1%, yield of E isomer: 47.3%) were confirmed.

EXAMPLE 4

To a mixture of 3-benzoylpyridine (1.65 g, 9 mmol), 5-carboxypentyltriphenylphosphonium bromide (4.2 g, 9.2 mmol) and tertiary amyl alcohol (15 ml) was added potassium tertiary butoxide (2.53 g, 198 mmol) by several portions with stirring and the reaction mixture was stirred at 20 to 30° C. for 2 hours. To the reaction solution were added water (50 ml) and toluene (30 ml) and layers were separated. (E)-and (Z)-7-phenyl-7-(3-pyridyl)-6-heptenoic acids in the aqueous layer were determined according to the same manner as that described in Example 1. As the results, 1.31 g of E isomer and 1.01 g of Z isomer (E:Z=56.3:43.7), total 2.32 g (yield: 91.7%, yield of E isomer: 51.6%) were confirmed.

EXAMPLE 5

To a mixture of 3-benzoylpyridine (1.65 g, 9 mmol), 5-carboxypentyltriphenylphosphonium bromide (4.2 g, 9.2 mmol), tertiary butanol (15 ml) and cyclohexane (5 ml) was added sodium hydride (60% in oil, 0.55 g, 13.5 mmol) by 3 to 4 portions with stirring under a $N_2$ atomosphere and stirred at 20° to 30° C. for 3 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as that described in Example 1. As the results, 1.14 g of E isomer and 1.12 g of Z isomer (E : Z=50.5:49.5 ), total 2.26 g (yield: 89.5%, yield of E isomer: 45.2%) were confirmed.

EXAMPLE 6

To a mixture of 3-benzoylpyridine (1.65 g, 9 mmol), 5-carboxypentyltriphenylphosphonium bromide (4.2 g, 9.2 mmol), tertiary butanol (15 ml) and isopropyl ether (5 ml) was added sodium hydride (60% in oil, 0.55 g, 13.5 mmol) by portions 3 to 4 times with stirring under a $N_2$ atmosphere and stirred at 20° to 30° C. for 3 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as that described in Example 1. As the results, 1.11 g of E isomer and 1.09 g of Z isomer (E:Z=50.7:49.3), total 2.20 g (yield: 87.1%, yield of E isomer: 44.2%) were confirmed.

Comparative Example 1

To a mixture of 3-benzoylpyridine (1.65 g, 9 mmol), 5-carboxypentyltriphenylphosphonium bromide (4.2 g, 9.2 mmol) and tetrahydrofuran (15 ml) was added sodium hydride (60% in oil, 0.55 g, 13.5 mmol) by 3 to 4 portions with stirring under a $N_2$ atmosphere and stirred at 20° to 30° C. for 3 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, 0.04 g of E isomer and 0.11 g of Z isomer (E:Z=26.7:73.3), total 0.15 g (yield: 0.6%, yield of E isomer: 0.16%) were confirmed.

When potassium tertiary butoxide was used as the base, the yield was 77.8%, E:Z=35.8:64.2 (yield of E isomer: 27.9%).

Comparative Example 2

To a mixture of 3-benzoylpyridine (1.65 g, 9 mmol), 5-carboxypentyltriphenylphosphonium bromide (4.2 g, 9.2 mmol) and isopropanol (15 ml) was added sodium hydride (60% in oil, 0.55 g, 13.5 mmol) by 3 to 4 portions with stirring under a N2 atmosphere and the mixture was stirred at about 80° C. for 3 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, 0.18 g of E isomer and 0.17 g of Z isomer (E:Z=51.0:49.0 ), total 0.35 g (yield: 13.9%, yield of E isomer: 7.1%) were confirmed.

Comparative Example 3

To a mixture of 3-benzoylpyridine (1.65 g, 90 mmol), 5-carboxypentyltriphenylphosphonium bromide (42.0 g, 92 mmol) and dimethylformamide (90 ml) was added sodium hydride (60% in oil, 8.0 g, 135 mmol) by portions with stirring at 30° to 35° C. under a $N_2$ atmosphere and the mixture was stirred at the same temperature for 3 hours. The reaction mixture was treated according the same manner as described in Example 2 and (E)- and (Z)-7-phenyl-7-(3-pyridyl)-6-heptenoic acids produced were determined by high performance liquid chromatography. As the results, 9.6 g of E isomer and 12.2 g of Z isomer (E:Z=44.2:55.8), total 21.8 g (yield: 86.0%, yield of E body: 38.8%) were confirmed.

When the reaction was carried out according to the same manner as described above by using dimethylsulfoxide instead of dimethylformamide, 9.6 g of E isomer and 10.8 g of Z isomer (E:Z=47.0:53.0), total 20.4 g (yield: 80.8%, yield of E isomer: 38.0%) were produced.

Comparative Example 4

To a mixture of 3-benzoylpyridine (1.65 g, 9 mmol), 5-carboxypentyltriphenylphosphonium bromide (4.2 g, 9.2 mmol) and dimethylformamide (15 ml) was added anhydrous potassium Carbonate (1.5 g, 11 mmol) with stirring and the mixture was stirred at 30° to 35° C. for 3 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, no formation of the objective product was observed.

Although similar experiments were carried out by using dimethylsulfoxide or tetrahydrofuran as the solvents no formation of the objective product was observed, either.

EXAMPLE 7

To a mixture of 3-benzoylpyridine (1.65 g, 9 mmol), 5-carboxypentyltriphenylphosphonium bromide (4.2 g, 9.2 mmol), tertiary butanol (12 ml) and toluene (12 ml) was added potassium tertiary butoxide (2.53 g, 1.98 mmol) by several portions with stirring and the mixture was stirred at 20° to 30° C. for 2 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, 1.18 g of E isomer and 0.94 g of Z isomer (E:Z=56.3: 43.7), total 2.12 g (yield: 90%, yield of E isomer: 50.8%) were confirmed.

EXAMPLE 8

To a mixture of 3-benzoylpyridine (1.65 g, 9 mmol), 5-carboxypentyltriphenylphosphonium bromide (4.2 g, 9.2 mmol) and tertiary butanol (15 ml) was added potassium tertiary butoxide (2.53 g, 1.98 mmol) by several portions with stirring and the mixture was stirred at 20° to 30° C. for 2 hours. To the reaction solution were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, 1.29 g of E isomer and 0.97 g of Z isomer (E:Z=57.0:4 .0), total 2.26 g (yield: 92.6%, yield of E isomer: 52.8%) were confirmed.

Comparative Example 5

To a mixture of 3-benzoylpyridine (1.65 g, 9 mmol), 5-carboxypentyltriphenylphosphoreum bromide (4.2 g, 9.2 mmol) and tetrahydrofuran (10 ml) was added dropwise n-butyl lithium (13.8 ml, 1.6 mol hexane solution) with stirring under a $N_2$ atmosphere and the mixture was stirred at 20° to 30° C. for 2 hours. To the reaction mixture were added water (50 ml) and toluene (30 ml) and layers were separated. (E)- and (Z)-7-phenyl-7-(3-pyridyl)-6-heptenoic acids in the aqueous layer were determined according to the same manner as described in Example 1. As the results, 2.5 mg of E isomer and 22.8 mg of Z isomer [E:Z=9.8:90.2), total 25.3 mg (yield: 1%, yield of E isomer: 0.1%) were confirmed.

EXAMPLE 9

To a mixture of 3-benzoylpyridine (22.0 g, 0.12 mol), 5-pentyltriphenylphosphonium bromide (49.6 g, 0.12 mol), tertiary butanol (210 ml) and toluene (70 ml) was added potassium tertiary butoxide (26.9 g, 0.24 mol) with stirring under a $N_2$ atmosphere, while maintaining at 3° to 10° C. After stirring at 3° to 10° C. for 1 hour and then at 24 to 25° C. for 1 hours, water (2 ml) was added and the mixture was concentrated under reduced pressure. The residue was dissolved in toluene (200 ml) and washed with water (200 ml×4). The organic layer was concentrated under reduced pressure. When the residue was subjected to high performance liquid chromatography to determine the ratio of the E and Z isomers, it was found that the ratio (E:Z) was 58:42. To the residue was added n-hexane (150 ml) and the mixture was allowed to stand overnight. The resulting precipitated triphenylphosphine oxide was filtered off. The mother liquor was concentrated under reduced pressure and the residue was subjected to silica gel chromatography to separate E and Z isomers. Z isomer was firstly eluted and, subsequently, E isomer was eluted. The fractions containing E isomer and Z isomer, respectively, were distilled under reduced pressure to obtain Z isomer (136°14 138° C./0.3 mmHg) (6.5 g), E isomer (136°–138° C./0.3 mmHg) (5.9 g) and a mixture of E and Z isomers (9.8 g).

Z isomer: (Z)-6-phenyl-6-(3-pyridyl)-5-hexene
E isomer: (E)-6-phenyl-6-(3-pyridyl)-5-hexene
NMR
Z isomer: 8.47 (2H, m), 7.22 (7H, m), 6.18 (1H, t), 2.12 (2H, m), 1.39 (4H, m), 0.85 (3H, t)
E isomer: 8.53 (1H, d), 8.44 (1H, dd), 7.30 (4H, m), 7.15 (3H, m), 6.12 (1H, t), 2.15 (2H, m), 1.38 (4H, m), 0.86 (3H, t)

EXAMPLE 10

To a mixture of 3-(3,4-methylenedioxybenzoyl)pyridine (3.0 g, 13.2 mmol), 5-carboxypentyltriphenylphosphonium bromide (6.2 g, 13.6 mmol), tertiary butanol (42 ml) and toluene (18 ml) was added potassium tertiary butoxide (3.3 g, 29 mmol) with stirring under a $N_2$ atmosphere, while maintaining at 3° to 10° C. After stirring at 3° to 10° C. for 1 hour and then 20° to 30° C. for 1 hour, the mixture was concentrated under reduced pressure and water (60 ml) was added. After washing with toluene (30 ml×2), the aqueous layer was adjusted to pH 5.5. The aqueous layer was extracted with ethyl acetate (60 ml) and the organic layer was concentrated under reduced pressure. When the residue was subjected to high performance liquid chromatography to determine the ratio of E and Z isomers, it was found that the ratio (E:Z) was 52:48. The residue was subjected to silica gel chromatography and eluted with ethyl acetate to collect a fraction containing Z isomer. The eluate was concentrated. The residue was treated with ethyl acetate-isopropyl ether to obtained crystals of Z isomer (0.65 g, 14.7%). On the ether hand a fraction containing a large amount of E isomer was collected and the fraction was concentrated. A part of the residue (100 mg) was subjected to high performance liquid chromatography (column: YMC, ODS column 20×250 mm; mobile phase: methanol:0.05M potassium dihydrogen phosphate=3:2) to obtain E isomer (55 mg, oil).

Z isomer: (Z)-7-(3,4-methylenedioxyphenyl)-7-(3-pyridyl)-6-heptenoic acid
E isomer: (E)-7-(3,4-methylenedioxyphenyl)-7-(3-pyridyl)-6-heptenoic acid
Melting point
Z isomer: 8920°–91° C.
NMR
Z isomer: 9.20 (COOH), 8.46 (2H, m), 7.50 (1H , m), 7.30 (1H, m), 6.86 (1H, d), 6.68 (1H, d), 6.53 (1H, dd), 6.05 (1H, t), 5.92 (2H, s), 2.28 (2H, m), 1.57 (4H, m)
E isomer: 10.30 (COOH), 8.50 (2H, m), 7.47 (2H, m), 6.80 (1H, d), 6.60 (1H, dd), 6.57 (1H, d), 6.06 (1H, t), 5.96 (2H, s), 2.31 (2H, m), 2.16 (2H, m), 1.58 (4H, m)

EXAMPLE 11

To a mixture of 3-benzoylpyridine (3.9 g, 10 mmol), 5-ethoxycarbonylpentyltriphenylphosphonium bromide (10.0 g, 10 mmol), tertiary butanol (70 ml) and toluene (30 ml) was added potassium tertiary butoxide (2.3 g, 10 mmol) with stirring under a $N_2$ atmosphere, while maintaining at 0° to 5° C. After stirring at 0° to 5° C. for 1 hour and then 20° to 25° C. for 1 hour, the mixture was concentrated under reduced pressure. The residue was dissolved in toluene (100 ml) and washed with water (100 ml x 2) and then the organic layer was concentrated under reduced pressure. By using ethyl esters derived from (E)-7-phenyl-7-(3-pyridyl)-6-heptenoic acid and (E,Z)-7-phenyl-7-(3-pyridyl)-6-heptenoic acid, respectively, as authentic samples, the residue was subjected to high performance liquid chromatography to determine the ratio of E and Z isomers. As the result, the ratio (E:Z) was 62:38.

E isomer: (E)-7-phenyl-7-(3-pyridyl)-6-heptenoic acid

NMR

Authentic sample of E isomer: 8.51 (1H, d), 8.43 (1H, q), 7.20 (7H, m), 6.10 (1H, t), 4.11 (2H, q), 2.15 (2H, m), 1.60 (2H, m), 1.23 (3H, t)

EXAMPLE 12

A mixture of potassium hydroxide (1.0 g, 18.4 mmol) and tertiary butanol (50 ml) was heated to 85° to 90° C. and about 35 ml of a mixture of tertiary butanol and water was distilled off. To the residue was added toluene (5 ml), and to the mixture were added 3-benzoylpyridine (1.65 g, 9 mmol), 5-carboxypentyltriphenylphosphonium bromide (4.2 g, 9.2 mmol) in several portions at 5° to 10° C. After completion of addition, the mixture was stirred at 5° to 10° C. for 2 hours. To the reaction mixture was added water (50 ml) and toluene (30 ml), and layers were separated. (E)- and (Z)-7-phenyl-7-(3-pyridyl)-6-heptenoic acids in the aqueous layer were determined by high performance liquid chromatography with authentic samples of E isomer and Z isomer. As the results, it was confirmed that 1.36 g of E isomer and 0.89 g of Z isomer E:Z=60.5:39.5), total 2.25 g (yield: 89.0%, yield of E isomer: 53.8 %) were contained.

What is claimed is:

1. A process for producing a substituted vinyl pyridine compound of the formula:

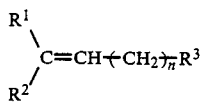   (I)

wherein
$R^1$ is pyridyl;
$R^2$ is a phenyl unsubstituted or substituted by methylenedioxy;
$R^3$ is ($C_1$–$C_4$) alkyl,
hydroxymethyl,
2-tetrahydropyranyloxymethyl,
2-tetrahydrofuryloxymethyl,
an acyloxymethyl of the formula $R_4COOCH_2$—
wherein $R^4$ is hydrogen
($C_1$–$C_6$) alkyl or pyridyl,
halogenomethyl,
($C_2$–$C_5$) alkoxymethyl,
cyano,
carbamoyl,
a group of the formula $R_5R_6N$—CO—
wherein $R^5$ and $R^6$ each is
($C_1$–$C_6$) alkyl or
phenyl, methylphenyl or dimethylphenyl, carboxyl or a ($C_2$–$C_5$) alkoxycarbonyl and
n is an integer of 1 to 22,
which comprises reacting a compound of the formula

   (II)

wherein $R^1$ and $R^2$ are as defined above, with a compound of the formula

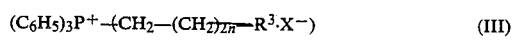   (III)

wherein $R^3$ is as defined above; and X is a halogen atom, in a tertiary alcohol in the presence of a metallic hydride or a tertiary alkoxide of an alkali metal.

2. A process according to claim 1, wherein the reaction is carried out under the atmosphere of a dried inert gas.

3. A process according to claim 1, wherein the reaction is carried out in the presence of a hydride of an alkali metal or an alkaline earth metal, or a tertiary butoxide of an alkali metal.

4. A process according to claim 1, wherein the metallic hydride or a tertiary alkoxide of an alkali metal is used in an amount of 2.0 to 3.0-fold mol as much as that of the compound (III).

5. A process according to claim 1, wherein the tertiary alcohol is tertiary-butanol or tertiary amyl alcohol.

6. A process according to claim 1, wherein the tertiary alcohol is used in combination with another solvent selected from group consisting of an aromatic hydrocarbons, aliphatic saturated hydrocarbon or an aliphatic ether.

7. A process according to claim 6, wherein the other solvent is toluene, benzene, isopropyl ether or cyclohexane.

8. A process according to claim 6, wherein the reaction is carried out by using tertiary-butanol and toluene.

9. A process according to claim 1, wherein $R^1$ is 3-pyridyl.

10. A process according to claim 1, wherein $R^2$ is phenyl.

11. A process according to claim 1, wherein $R^3$ is carboxyl, a lower alkoxycarbonyl group or methyl.

12. A process according to claim 1, wherein n is an integer of 3 to 8.

13. A process according to claim 12, wherein n is an integer of 3 to 6.

* * * * *